United States Patent
Dinkelacker

[11] Patent Number: 6,164,969
[45] Date of Patent: Dec. 26, 2000

[54] DENTAL IMPLANT

[76] Inventor: Wolfgang Dinkelacker, Mercedesstrasse 9/1, D-71063 Sindelfingen, Germany

[21] Appl. No.: 09/155,862

[22] PCT Filed: Mar. 21, 1997

[86] PCT No.: PCT/EP98/01472

§ 371 Date: Oct. 1, 1998

§ 102(e) Date: Oct. 1, 1998

[87] PCT Pub. No.: WO98/42273

PCT Pub. Date: Oct. 1, 1998

[30] Foreign Application Priority Data

Mar. 21, 1997 [EP] European Pat. Off. .............. 97104836

[51] Int. Cl.[7] .................................................... A61C 8/00
[52] U.S. Cl. ................................................................ 433/173
[58] Field of Search .................... 433/173, 174, 433/172

[56] References Cited

U.S. PATENT DOCUMENTS

| | | | |
|---|---|---|---|
| 3,905,109 | 9/1975 | Cohen et al. | 433/174 |
| 4,468,200 | 8/1984 | Munch | 433/174 |
| 5,009,596 | 4/1991 | Soderberg | 433/174 |

FOREIGN PATENT DOCUMENTS

| | | |
|---|---|---|
| 2720624 | 12/1995 | France . |
| 39 17 690 | 12/1990 | Germany . |
| 40 28 855 | 12/1992 | Germany . |
| 195 09 762 | 9/1996 | Germany . |
| WO 95/21589 | 8/1995 | WIPO . |

*Primary Examiner*—Ralph A. Lewis
*Attorney, Agent, or Firm*—Kudirka & Jobse, LLP

[57] ABSTRACT

A dental implant has a two-sided taper of the head part which is formed by bevels tapering down on both sides of the threaded bore toward the edges of the jaw bone. The bevels form lines of intersection with the circumference of the head part, starting from the edge areas of an end face of the head part and running at a variable height, corresponding to the shape of the upper edges of the jaw bone. A contact body connected to the crown is adapted to the taper at the upper edge of the head of the implant. The two-sided taper may be asymmetrical in design. The surface of the contact body facing the crown corresponds in shape to the head part and has bevels with a corresponding complementary shape. This yields a simplified prosthetic system with integrated security against twisting which has improved mechanical stability in both buccal and lingual directions.

18 Claims, 6 Drawing Sheets

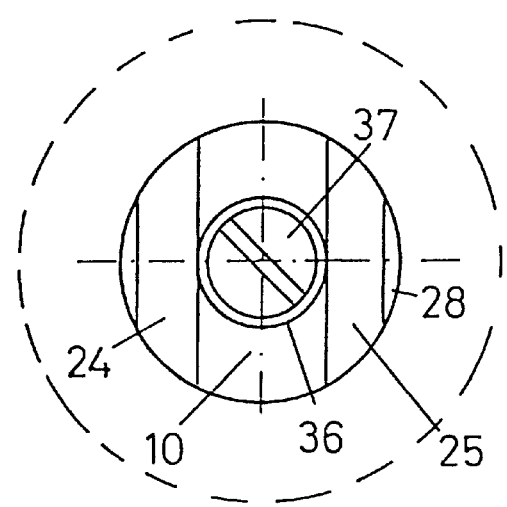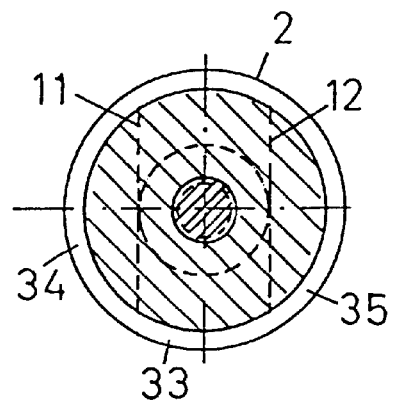
FIGURE 6  FIGURE 7
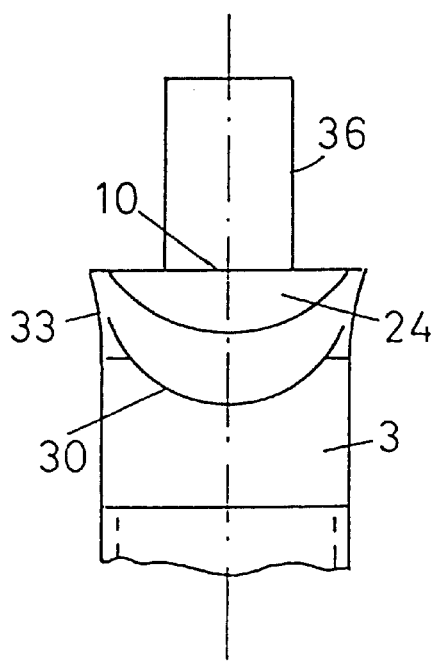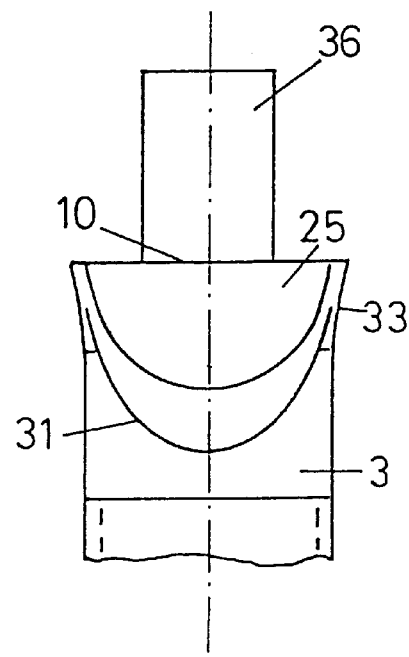
FIGURE 8  FIGURE 9

DENTAL IMPLANT

SCOPE OF THE INVENTION

The invention relates to an enosseous dental implant which includes a rotationally symmetrical bottom part, a head part and a threaded bore emanating from the head part to accommodate a fastening screw for fastening directly or through a intermediate member a dental crown, and which includes a device for securing the dental crown against twisting on the head part.

STATE OF THE ART

There are known dental implants for a tight-fitting denture consisting of a cylindrical or conical base body having a recess suitable for ingrowth in the jaw on its outside diameter, such as a roughened surface, cylindrical or conical thread, stepped grooves and the like. The head of the implant is polished and has a central bore which is designed as a threaded hole and serves to receive a threaded pin on which the crown is attached (German Patent No 40 28 855 C2, German Patent No. 39 17 690 C2). The crown is secured against twisting by a device connected to the fixation, such as a square or elliptical fitting. The crown is supported in a plane on the implant There is no adaptation of the implant the natural shape of the bone.

It is also known that a spacer sleeve which can be provided between the crown and the head of the implant has a peripheral shoulder on its circumference to which the lower edge of the crown is attached (German Patent application DE-A 195 09 762) The shoulder runs at an inclined angle to the upper edge of the implant head at a distance that varies over its circumference, to thereby achieve an improved adaptation of the transition between the crown and the implant to the anatomical conditions through an appropriate choice of the base height of the shoulder The spacer sleeve here serves as the implant head. It is designed so that it is closed at the bottom and is screwed into the base body of the implant by a thread and it has a central threaded bore to accommodate the threaded pin to which the crown is attached. A centering collar on the lower end of the spacer sleeve is provided with vertical projections which engage in corresponding recesses in the base body and serve to orient the crown and secure it against twisting.

Again with this device, the crown is again supported in one plane without adapting to the natural shape of the bone.

SUMMARY OF THE INVENTION

The dental implant according to the invention, as defined in the patent claims, provides for a two-sided taper of the head part which is formed by bevels arranged on both sides of the threaded bore and extending crosswise to the direction of the row of teeth. The bevels form lines of intersection with the circumference of the head part, emanating from the edge areas of an end face of the head part and running at a variable height, corresponding to the shape of the upper edges of the jaw bone. A contact body connected to the crown is adapted to the taper at the upper edge of the head of the implant.

The two-sided taper may be asymmetrical in design. For this purpose, an shallower bevel is provided on the lingual side and a steeper bevel is provided on the bucal side. Lines of intersection of the different bevels with the circumference of the head part extend in this embodiment on both sidles at different heights in accordance with the shape of the jaw bone.

The implant according to the invention permits an improved adaptation to the anatomy of the jaw bone as well as the soft tissue above the bone. Due to the shape of the implant, an adaptation to differences in level between the buccal and lingual heights and the approximate height of the bone is achieved, and a natural upper edge of the jaw bone is reproduced. In this way it is possible to avoid removing of bone tissue to establish a uniform base for the prosthetic system, and the natural bone shape can be mostly preserved and can regrow when the implant heals in. Furthermore, the nature shape of the bone determines the natural shape of the soft tissue, so that an interimplant papillary structure develops.

The shape of the head of the implant, adapted to the differences in level in the bone, prevents circular inflammation. Osteolysis develops on a different level, as is also the case with a normal tooth.

In addition, this arrangement has a positive effect on controlled bone regeneration when using the membrane technique. Due to the tapered head of the implant, the membrane conforms to the shape of the head of the implant, and folding is prevented in applying the membrane.

The surface of the contact body facing the crown corresponds in shape to the head part and has bevels with a corresponding complementary shape. This yields a simplified prosthetic system with integrated security against twisting which has improved mechanical stability in both buccal and lingual directions. The bevels on the head of the implant and the corresponding bevels on the contact body absorb the forces acting laterally on the implant and prevent shearing forces from occurring in the area of the securing screw.

DESCRIPTION OF THE DRAWINGS

Various embodiments of this invention are described below on the basis of drawings, which show:

FIG. 6: a section according to line A—A in FIG. 2;

FIG. 7: a section according to line B—B in FIG. 2;

FIG. 8: a view of the contact body 10 from direction C in FIG. 2;

FIG. 9: a view of the contact body 10 from direction D in FIG. 2;

DETAILED DESCRIPTION OF THE EMBODIMENT ILLUSTRATED IN FIGS. 1 THROUGH 9

Figure 1:
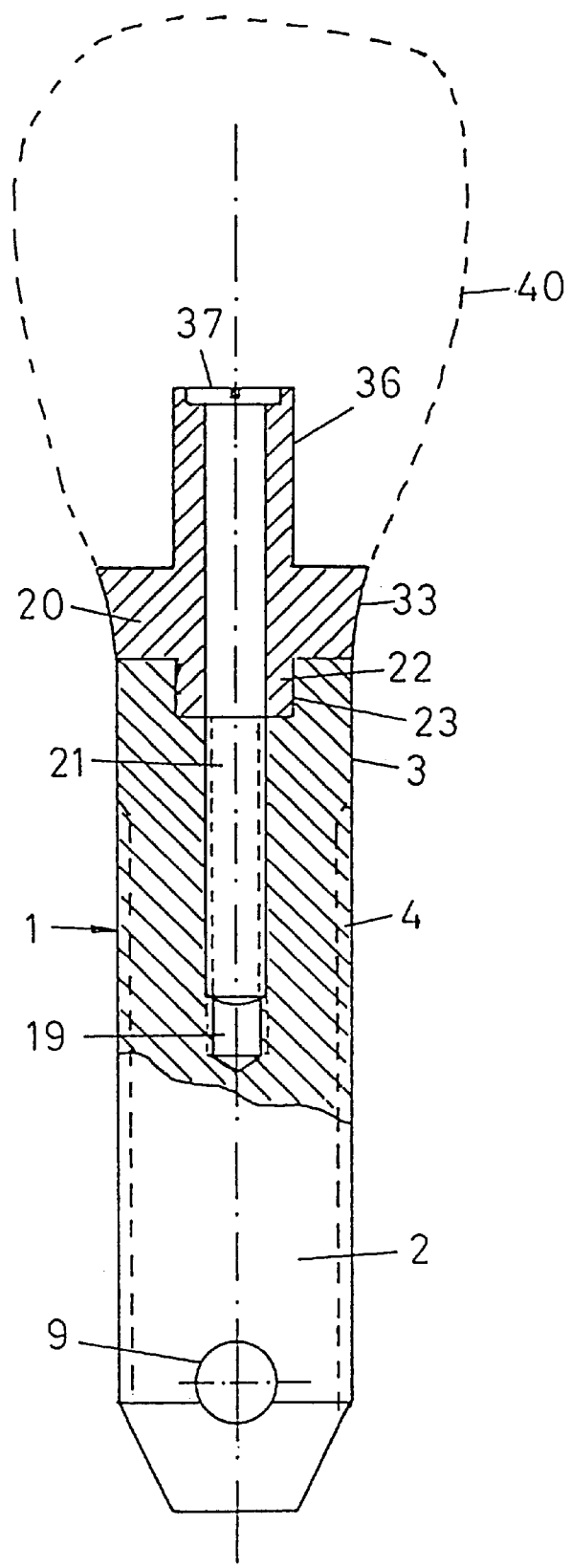
FIG. 1: an embodiment of the dental implant according to this invention in a sectional diagram with the line of intersection running along the longitudinal axis of the dental implant.
Figure 2:
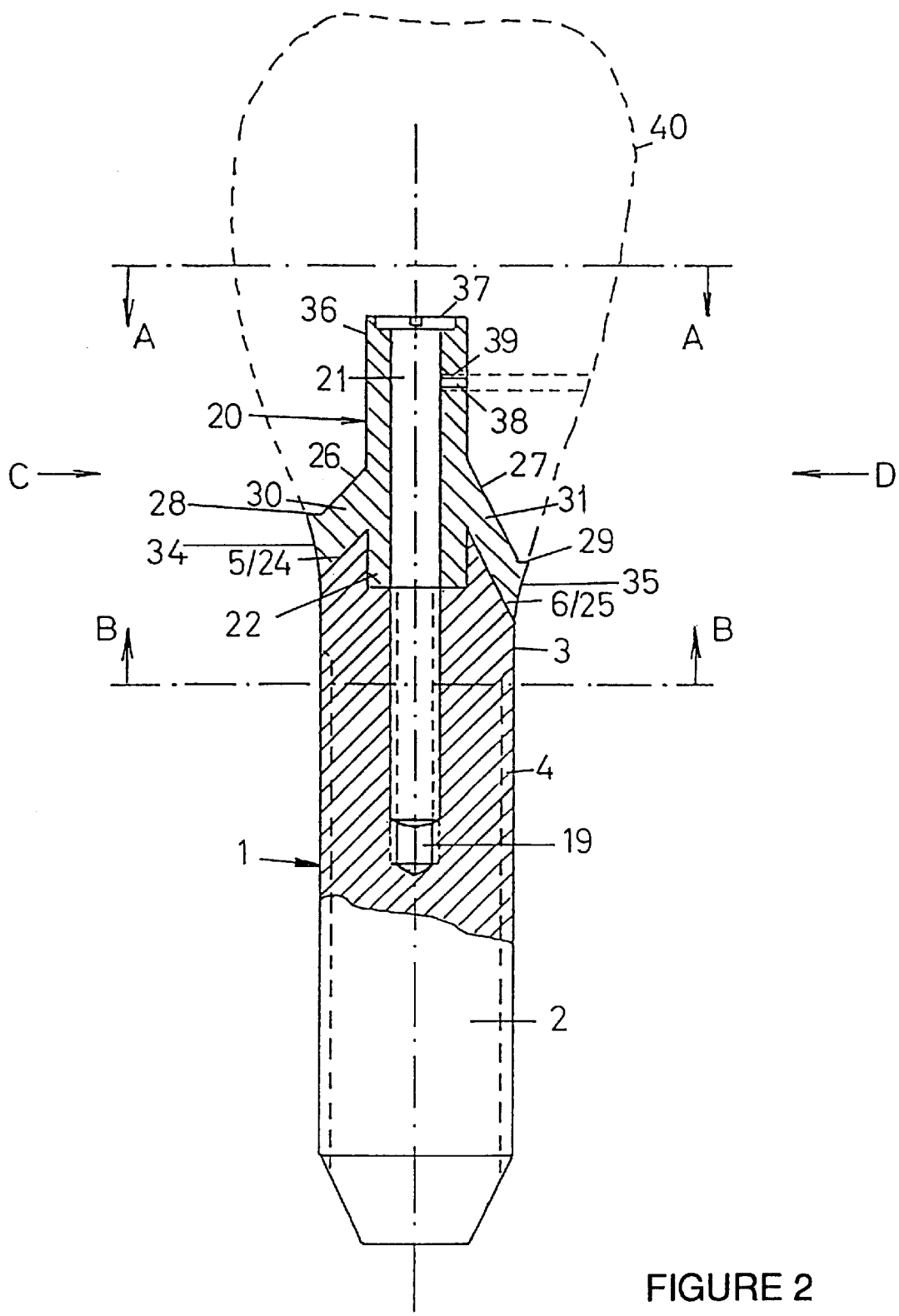
FIG. 2: another sectional diagram of the dental implant from FIG. 1 with the line of intersection running at a 90° offset.

The embodiment illustrated here shows an enosseous dental implant having a cylindrical implant body 1 which consists of an implant root 2 and an implant head 3. Implant head 3 and implant root 2 may be designed in one piece, as shown in the figures, or may consist of two parts that are joined together in a suitable manner. On its perimeter, the implant root 2 is provided with a thread 4 with which the implant is screwed into a predrilled hole in the jaw bone.

A passage 9 on the lower end of the implant root 2 serves to facilitate settling and healing of the implant in the bone. When inserted, the top edge of the jaw bone runs in the area of the implant head 3. As shown by FIGS. 2 through 5, the implant head 3 has on its top end a two-sided taper formed by bevels 5 and 6. Due to this design, the top end of implant head 3 is adapted to the shape of the jaw bone.

Figure 3:
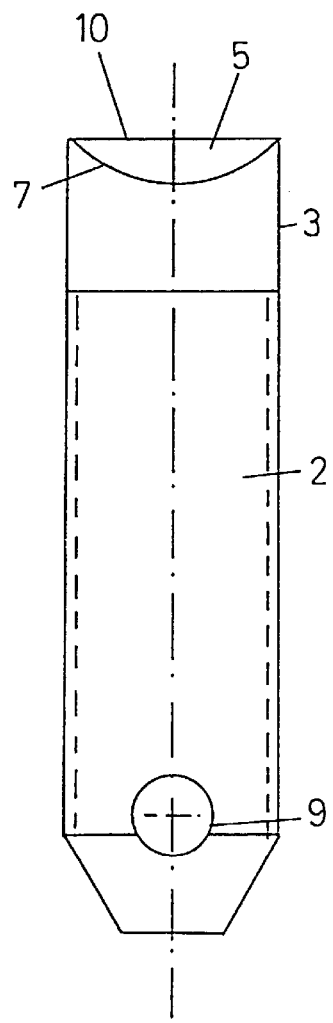
FIG. 3: a view of the implant head 1 from the lingual side.
Figure 4:
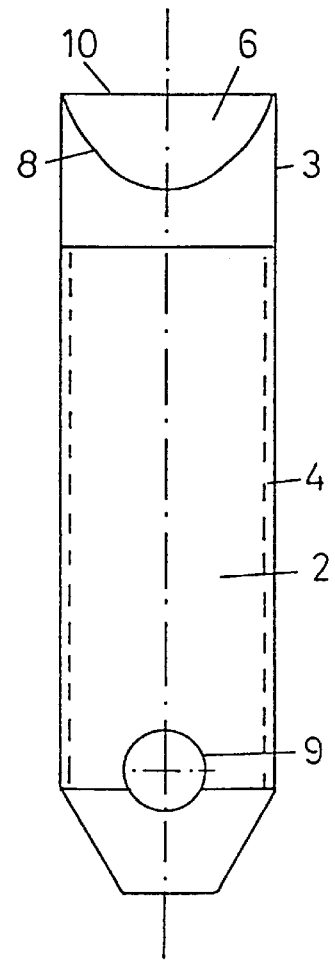
FIG. 4: a view of the implant body 1 from the buccal side.

Bevels 5 and 6 are asymmetrical in design. Therefore, bevel on the lingual side of the inserted implant runs at a shallower angle than the bevel 6 on its opposite side. Bevel 6 thus forms a more acute angle with the longitudinal axis of the implant body 1 than does the bevel 5, thus forming arc-shaped lines of intersection 7 and 8 with the cylindrical circumference of head part 3, running at different heights on both sides of the implant head 3 (FIGS. 3 and 4). In this way, the edge of the implant facing the crown can be largely adapted to the different shape of the edge of the jaw bone on the lingual and buccal sides.

Figure 5:
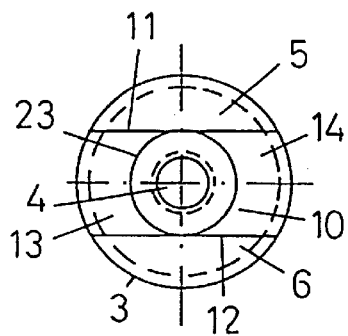
FIG. 5: a top view of the implant body according to FIGS. 3 and 4.

The top view in FIG. 5 shows that the bevels 5, 6 form straight top edges 11, 12 with the end face 10 of the implant head. When the implant is inserted, the edge areas 13 and 14 of end face 10 are approximately at the level of the upper edge of the jaw bone between adjacent teeth and thus are at a different distance from the lines of intersection 7, 8 forming bevels 5, 6.

After the healing and settling phase, a contact body 20 is placed on implant head 3 and is held in this position by a threaded pin 21 which is screwed into a concentric threaded hole 19 in the implant root (FIGS. 1 and 3). The contact body 20 has a guide part 22 which in this embodiment is designed as a cylinder that engages in a corresponding recess 23 in the implant head 3. The lower side of the contact body 20 is adapted with a shape that is complementary to the asymmetrical shape of the implant head. For this purpose, on both sides of the guide cylinder 22, the contact body 20 has inclined faces 24, 25 that correspond to the bevels 5 and 6 on implant head 3 and are in form-fitting contact with them. The faces 24, 25 also serve as security against axial twisting of contact body 20 with respect to implant body 1.

The top side of the contact body also has a corresponding design. The angular position of the inclined top faces 26, 27 corresponds to that of the inclined bottom faces 24, 25. The outer end of faces 26 runs out in a horizontal collar 28. A corresponding collar 29 is also on the outer end of the inclined face 27. Faces 24 and 26 border an apron 30 with a downward slope 30 (FIG. 8), and faces 25 and 27 border an apron 31 with a downward slope (FIG. 9). Aprons 30, 31 run in the cylindrical part 33 of the contact body 20 below the edge areas 13, 14 of the end-face 10. The circumference of the contact body 20 increases in a conical shape toward the top, while circumference 33 has a slightly concave profile. Likewise, the circumference of the contact body 20 increases toward the top in the area of the aprons 30, 31 with a slightly concave profile 34, 35, which develops into the circumference 33 of the contact body 20 without edges.

The contour of a crown 40 follows the slightly concave profile 33, 34, 35 without a joint or a shoulder. On its lower side, the crown 40 is adapted to the shape of the contact body 20 and is attached to it. An extension 36 of the contact body 20 having a shallow recess on its top end to accommodate the screw head 37 on pin 21 serves to orient and secure the crown 40. The extension 36 may be in the shape of a cylinder, as shown in the figures, or it may have a different shape such as the Shape of a pointed cone. The crown 40 is attached to the contact body 20 by cementing and/or by a transverse screw 38 which is guided through a hole in the crown and engages in a lateral threaded bore 39 in the extension 36 of the contact body 20.

Figure 10:
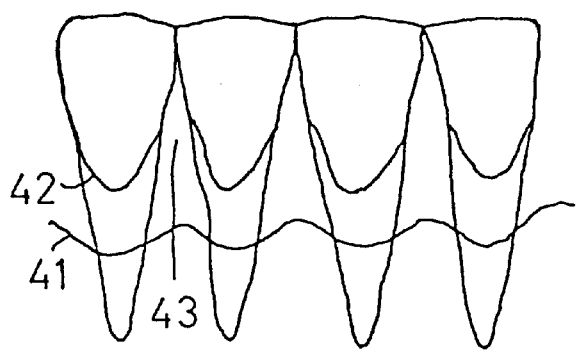
FIG. 10: a view of a natural dental arrangement.
Figure 11:
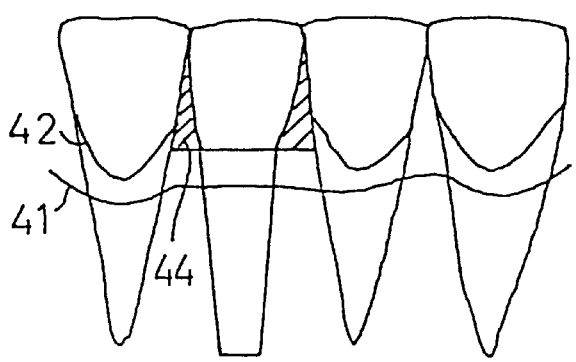
FIG. 11: a view of a traditional implant system.
Figure 12:
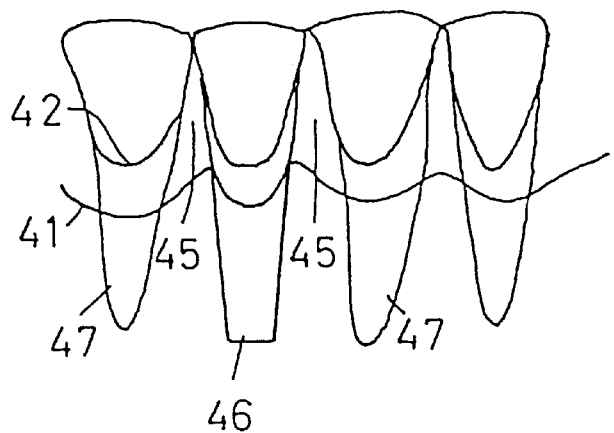
FIG. 12: a view of an implant system according to this invention.

The thickness of aprons 30, 31 is such that they correspond approximately to the thickness of the soft tissue which forms on the jaw bone. This yields an adaptation to the anatomical conditions even in the area of the soft tissue. The shape of the soft tissue is determined by the natural course to which the implant head is adapted by the two-sided tapered design of the head part, so that an interimplant papillary structure also develops postoperatively. FIG. 10 shows the shape of the bone 41 and the gingiva 42 as well as the interdental papillae 43 with a natural dental arrangement. The corresponding view of a dental arrangement with a traditional implant system shows the loss of interdental papillae in the areas 44 between the implant and the neighboring natural teeth. FIG. 12 shows the implant system according to FIGS. 1 and 8 with interdental papillae 45 between implant 46 and the neighboring natural teeth 47 which develops due to the adaptation of level to the natural shape of the bone and soft tissue.

ALTERNATIVE EMBODIMENTS

FIGS. 13 through 16 show alternative embodiments of the invention. In the embodiment according to FIG. 13, the asymmetrical taper of the implant head 50 on its upper end is achieved by beveled partial faces 51 and 52 with a convex curvature, developing into end face 53 of the implant head without an edge. The contact body (not shown) which belongs with this embodiment is adapted to the top and bottom sides of the shape of the implant head 50, as explained above.

Figure 14:
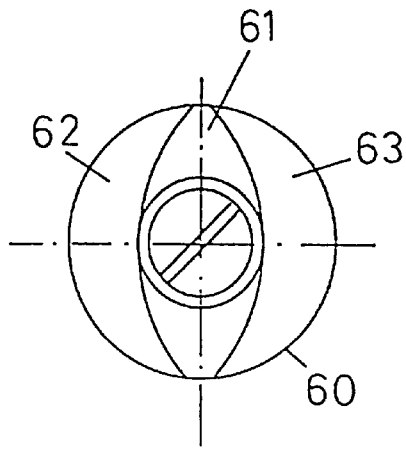
FIG. 14: a top view of another embodiment of the head of the implant according to this invention.

FIG. 14 shows that in another embodiment of this invention, the implant head 60 has an end face 61 with an approximately elliptical shape on its upper end derived from a convex curve of the asymmetrical beveled faces 62 and 63 in the radial direction. This permits an adaptation to particular anatomical conditions on the upper edge of the jaw bone. Again in this embodiment, the contact body (not shown) which belongs with it is adapted to the shape of the implant head 60 on its upper and lower sides.

Figure 16:
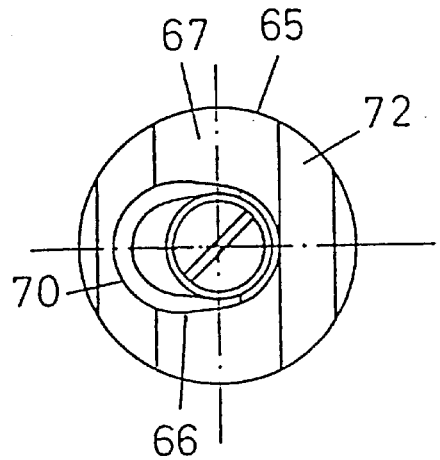
FIG. 16; a top view of the arrangement in FIG. 15.
Figure 13:
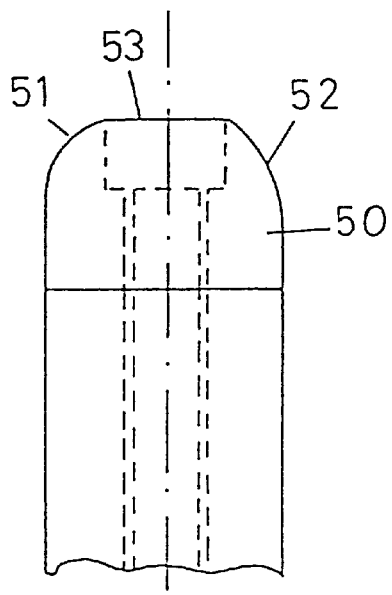
FIG. 13: a partial view of the head of the implant of an alternative embodiment of the invention.
Figure 15:
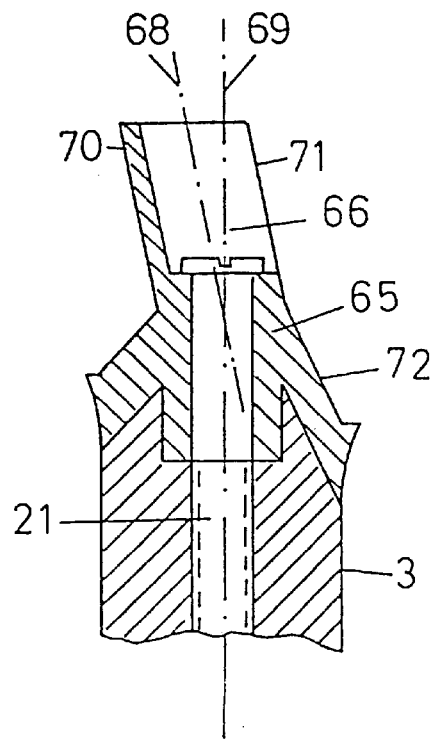
FIG. 15: a partial view of the contact body of another embodiment of this invention.

The top part of the contact body serving to secure the crown is to be adapted to the axial direction of the crown. FIGS. 15 and 16 show one embodiment where an extension 66 of a contact body 65 extending upward is bent at an acute angle to the axis 69 of the implant body in the direction of crown axis 68. The extension 66 is a friction body 70 which is designed concentric with crown axis 68 and is set on end face 67 of contact body 65, and is open toward the axis 69 and has an inclination 71 which runs into the inclined face 72 on the buccal side of the contact body 65. The crown is attached to the contact body 65 in the direction of axis 68. Any other shapes of the extension of the contact body projecting upward are also possible.

What is claimed is:

1. An enosseous dental implant which includes a rotationally symmetrical bottom part that defines an implant axis, a head part which has a periphery, a threaded bore therethrough to accommodate a fastening screw and an upper end having thereon bevels in the form of faces inclined toward one another, and a contact body which is connectable to a dental crown, has a lower side which mates with the inclined faces, and has a bore therethrough coaxial with the threaded bore to accommodate the fastening screw, characterized in that (a) the head part has an end face, extends to the periphery and intersects the bevels, the threaded bore emanating from the end face. extending axially toward the bottom part of the implant and accommodating the fastening screw;

(b) edge areas of the end face on both sides of the threaded bore between the bevels near the periphery determine a base level for the position of the dental implant and the crown; and (c) lines of intersection of the bevels with the head part periphery extend to variable levels which can be adapted to the shape of a jaw bon( into which the implant is inserted.

2. An implant according to claim 1, characterized in that the bevels are asymmetrically shaped and extend at different angles to the implant axis, the steeper angle of which is on the buccal side of an inserted implant, the asymmetrical bevels extending from the edges and intersecting the periphery at different longitudinal points and wherein the contact body lower side is adapted to male with the asymmetrical bevels.

3. An implant according to claim 1, characterized in that the bevels are flat faces.

4. An implant according to claim 1, characterized in that the bevels are convex faces in the axial direction.

5. An implant according to claim 1, characterized in that the bevels are faces convex in the radial direction and intersect the end face to form an approximately elliptical end face on the implant head.

6. An implant according to claim 1, characterized in that the contact body has on its top side a two-sided taper which corresponds in shape to the bevels of the head part and to which the dental crow is adapted to mate.

7. An implant according to claim 2, characterized in that the contact body has on its top side bevels arranged asymmetrically with respect to the implant axis, adapted in the angular position at least approximately to the asymmetrical bevels on the implant head.

8. An implant according to claim 7, characterized in that the asymmetrical faces on the bottom side and on the top side of the contact body form aprons of different inclinations, an apron intended to be located on the buccal side of an inserted implant body having a more acute angle of inclination to the implant axis than an apron intended to be located on the lingual side of an inserted implant body.

9. An implant according to claim 7, characterized in that the bevels on the top side of the contact body have a narrow collar running at least approximately at a right angle with respect to the axis of the implant on their lower edges.

10. An implant according to claim 1, characterized in that the contact body has a peripheral profile which becomes larger in conical shape toward the dental crown to increase the base for accommodating the dental crown and for a smooth adaptation to the periphery of the dental crown.

11. An implant according to claim 10, characterized in that the contact body has asymmetrical faces on the bottom side and on the top side which asymmetrical faces form aprons of different inclinations which aprons each have a peripheral area and wherein the increasing periphery of the contact body has a concave curvature which also extends over the peripheral area of the aprons.

12. An implant according to claim 1, characterized in that the contact body has a central bore to accommodate the fastening screw and a guide part which is adapted to a complementary recess in the implant body.

13. An implant according to claim 1, characterized in that the contact body has an extension upward that serves to secure the crown.

14. An implant according to claim 13, characterized in that the extension of the contact body is designed as a cylinder concentric with the axis of the implant.

15. An implant according to claim 13, characterized in that the extension of the contact body is designed as a cone arranged to be concentric with the axis of the implant.

16. An implant according to claim 13, characterized in that the extension of the contact body is designed to accommodate a transverse screw for attaching the dental crown.

17. An implant according to claim 13, characterized in that the extension of the contact body extends at an acute angle to the axis of the implant which angle is adapted to the axial position of a dental crown inclinedly attached to the implant body.

18. An implant according to claim 17, characterized in that the extension of the contact body is designed as a friction body which is concentric with an axis of the dental crown, projecting upward from the end face of the contact body and which is open toward the axis of the implant.

* * * * *

UNITED STATES PATENT AND TRADEMARK OFFICE
CERTIFICATE OF CORRECTION

PATENT NO. : 6,164,969
DATED : December 26, 2000
INVENTOR(S) : Wolfgang Dinkelacker It is certified that error appears in the above-identified patent and that said Letters Patent is hereby corrected as shown below:

Title page,
Item [22] PCT Filed: Replace "Mar. 21, 1997" with -- Mar. 13, 1998 --.

Signed and Sealed this

Twenty-third Day of October, 2001

Attest:

*Attesting Officer*

NICHOLAS P. GODICI
*Acting Director of the United States Patent and Trademark Office*